US00PP37336P2

(12) United States Plant Patent
Valstar

(10) Patent No.: US PP37,336 P2
(45) Date of Patent: Mar. 17, 2026

(54) ***CALATHEA* PLANT NAMED 'HGV25'**

(50) Latin Name: ***Calathea lietzei* E. Morren**
Varietal Denomination: HGV25

(71) Applicant: Gebr. Valstar Beheer B.V., Maasland (NL)

(72) Inventor: Oscar Valstar, Maasland (NL)

(73) Assignee: Gebr. Valstar Beheer B.V., Maasland (NL)

( * ) Notice: Subject to any disclaimer, the term of this patent is extended or adjusted under 35 U.S.C. 154(b) by 0 days.

(21) Appl. No.: 19/307,802

(22) Filed: Aug. 22, 2025

(51) Int. Cl.
*A01H 5/12* (2018.01)
*A01H 6/00* (2018.01)

(52) U.S. Cl.
USPC ..... Plt./375

(58) Field of Classification Search
USPC ..... Plt./375
See application file for complete search history.

*Primary Examiner* — Susan Mccormick Ewoldt
(74) *Attorney, Agent, or Firm* — Samuel R. McCoy, Jr.

(57) ABSTRACT

'HGV25' is a new and distinctive variety of *Calathea* plant which is characterized by having a broader growth habit when compared to other varieties of the same species, a green adaxial laminar surface with a variegation pattern consisting of a broadly and irregularly outlined midrib colored very light green to greyed-green and greyed-green striations along the interveinal areas of the distal half of the lamina, a dark greyed-purple lower foliar surface with which transitions to dark green towards the margins and an irregular greyed-orange ring present. 'HGV25' has shown to have the stability of all characteristics from generation to generation.

2 Drawing Sheets

Latin name of the genus and species: The Latin name of the genus and species of the novel variety disclosed herein is *Calathea lietzei* E. Morren.

Variety denomination: The inventive variety of *Calathea* disclosed herein has been given the variety denomination 'HGV25'.

BACKGROUND OF THE INVENTION

Parentage: The new plant originated as a spontaneous, partial plant, branch mutation. The mutation was discovered at a commercial greenhouse in Maasland, The Netherlands, in May of 2019, growing amongst a plurality of cultivated *Calathea lietzei* plant (not patented). The mutation exhibited conspicuously variegated foliage. Said branch mutation was subsequently harvested from the parent plant, rooted in a nursery container, and grown to maturity to evaluate the distinctness and stability of the characteristics first observed. Upon confirmation of its distinctness and stability, the new *Calathea* plant was selected for commercialization and given the name 'HGV25' in March 2020.

Asexual Reproduction: Asexual reproduction of 'HGV25' through vegetative division was first performed in May of 2019 at a commercial greenhouse in Maasland, Netherlands. Through four generations produced, 'HGV25' has shown that the unique features of the instant cultivar are stable and reproduced true to type.

SUMMARY OF THE INVENTION

The cultivar has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Calathea* cultivar 'HGV25'. These traits, in combination, distinguish 'HGV25' as a new and distinct cultivar.

1. *Calathea* 'HGV25' exhibits a green adaxial laminar surface with a variegation pattern consisting of a broadly and irregularly outlined midrib colored very light green to greyed-green and greyed-green striations along the interveinal areas of the distal half of the lamina; and
2. *Calathea* 'HGV25' exhibits a broader growth habit when compared to other varieties of the species; and
3. *Calathea* 'HGV25' exhibits a dark greyed-purple abaxial laminar surface which transitions to dark green towards the margins and apex with an irregular, yet conspicuous, greyed-orange ring.

BOTANICAL DESCRIPTION OF THE PLANT

Figure 1:
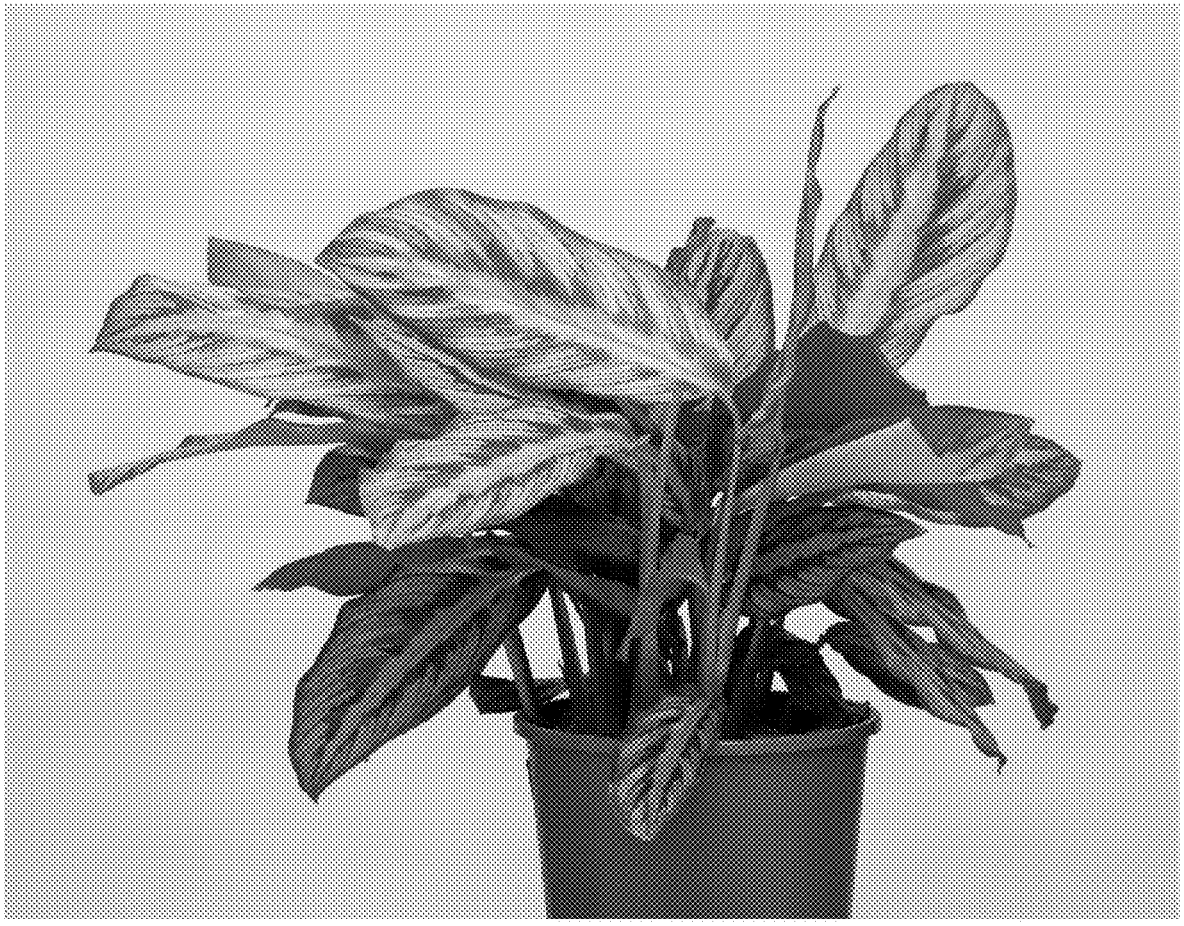
FIG. 1 shows, as nearly true as it is reasonably possible to make the same in color illustrations of this type, an exemplary 'HGV25' plant at approximately 12-month-old, potted into a 12 cm nursery container, grown in a greenhouse in Maasland, the Netherlands.
Figure 2:
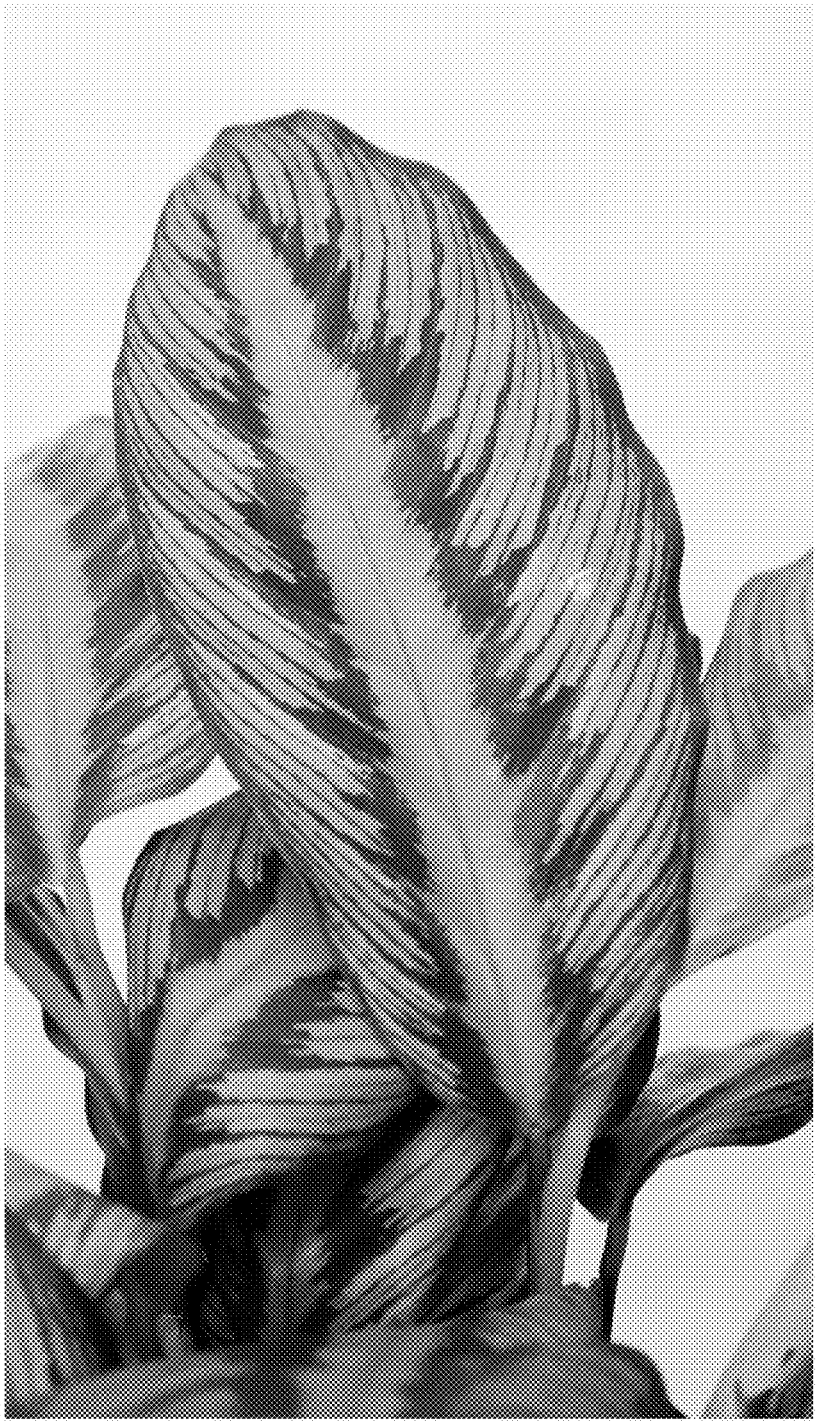
FIG. 2 shows, as nearly true as it is reasonably possible to make the same in color illustrations of this type, the typical foliage of a mature 'HGV25'.

The following is a detailed botanical description of a new and distinct variety of *Calathea* known as 'HGV25', based upon observations of plants, approximately one year old from a rooted cutting, grown in 12 cm nursery container in a climate-controlled greenhouse in Maasland, the Netherlands. Observation data was recorded in March of 2024. Plants were produced using conventional greenhouse production protocols for *Calathea* sp. which consisted of growing under shade with regular overhead irrigation. No pest control measures were utilized, and no photoperiodic treatments or artificial light was given to the plants.

Those skilled in the art will appreciate that certain characteristics will vary with older or, conversely, with younger plants. 'HGV25' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2019 Reprint.

A botanical description of 'HGV25' and comparisons with the parent and the most similar variety of common knowledge are provided below.

Plant description:

*Growth habit*.—Basally clump-forming, upright, non-flowering perennial.

*Plant profile*.—Broad flattened obovate.

*Height from soil level to the top of the foliar plane*.—18.1 cm, on average.

*Plant diameter*.—33.1 cm, on average.

*Environmental tolerances*.—USDA Zones 11 to 12; at least tolerant of temperatures as low as 8 degrees Celsius and up to 40 degrees Celsius.

Root system:

*Branching habit*.—Rhizomatous with rhizomes bearing a moderately dense network of feeder roots.

*Distribution*.—Roots are relatively shallow.

*Texture*.—Fibrous; non-fleshy.

*Color*.—Grey-brown, RHS 199D.

Stems:

*Branching characteristics*.—Basal foliage emerges directly from the base of the plant; no lateral branching.

*Number of basal shoots*.—7.

Foliage:

*Arrangement*.—Alternate.

*Division*.—Simple.

*Attachment*.—Petiolate.

*Quantity of leaves per shoot*.—Average of 2.

*Quantity of shoots per plant*.—Average of 8.

*Quantity of leaves per plant*.—Average of 15.

*Lamina*.—Shape — Elliptic to ovate. Length — 14.2 cm, on average. Width — 6.1 cm, on average. Apex — Acute. Base — Rounded to shallow truncate. Aspect — Slightly to moderately carinate. Attitude — Parallel to horizontal to slightly facing downward. Margin — Entire; moderate undulation. Texture and luster, adaxial surface — Smooth, glabrous, and slightly glossy. Texture and luster, abaxial surface — Smooth, glabrous, and matte. Color — Juvenile color, adaxial surface — Green, RHS 143A, with green adjacent to the main vein and along the interveinal areas of the distal half of the lamina, a blend of RHS 138B and 138C; margined green, RHS 143A. Juvenile color, abaxial surface — Green, RHS 138B with green, adjacent to the main vein and along the interveinal areas of the distal half of the lamina, RHS 138C; margined green, RHS 138B. Mature color, adaxial surface — Green, a blend of RHS NN137A and 139A, with a blend of very light green and greyed-green adjacent to the main vein, RHS N138C and 191B, and greyed-green along the interveinal areas of the distal half of the lamina, RHS 191B; margined green, RHS NN137A and 147B. Mature color, abaxial surface — Greyed-green, nearest to RHS 191A.

*Venation*.—Vein pattern — Pinnate. Vein color, adaxial surface — Midrib is colored yellow-green, nearest to RHS N144C, whereas the lateral veins are colored green, nearest to RHS 137B. Vein color, abaxial surface — Midrib is colored yellow-green, nearest to a blend of RHS 144A and 146B, transitioning to 151A proximally; ultimately becoming greyed-green, nearest to RHS 189A.

*Petiole, including geniculum*.—Length — Approximately 8.1 cm. Width — Approximately 0.25 cm at the proximal end and 0.3 cm at the distal end. Strength — Medium. Texture and luster, adaxial and abaxial surface — Both the adaxial and abaxial surface of the petiole are smooth, glabrous, and slightly glossy. Color, adaxial surface — Brown, nearest to RHS 200C. Color, abaxial surface — Brown, nearest to RHS 200C.

*Petiole wings*.—Length — 7.0 cm, on average. Width — 0.4 cm, on average. Texture and luster, adaxial and abaxial surface — Glabrous, slightly glossy. Color, adaxial surface — Transparent greyed-purple, nearest to RHS 183D, transitioning to yellow — green, nearest to RHS 145A, distally to the point of attachment. Color, abaxial surface — Transparent greyed-orange, nearest to RHS 177B.

*Geniculum*.—Length — Approximately 0.8 cm. Width — Approximately 0.3 cm. Color, adaxial surface — Brown, nearest to RHS 200D. Color, abaxial surface- — Yellow-green, nearest to RHS 146A.

*Sheath*.—Shape — Lanceolate, folded around the base of the leaf. Apex — Shallow premorse. Base — Broad cuneate. Length — 6.8 cm, on average. Width — Approximately 0.6 cm. Texture — Glossy, densely packed with short strigose pubescence, averaging in length at 1.0 mm; color almost indistinguishable from surrounding area but closest to greyed-brown RHS 199B. Color — Greyed-green, nearest to RHS 197A, transitioning to yellow-green nearest to RHS 148A, proximally to the point of attachment.

Inflorescence: No flowers observed to date.

Flower bud: No flowers observed to date.

Flower: No flowers observed to date.

Reproductive organs: No flowers observed to date.

Seed and fruit: No flowers observed to date.

Comparisons with the parent plant: Plants of the new cultivar 'HGV25' differ from its parent, an undisclosed unnamed *Calathea lietzei* plant (not patented), by the characteristics described in Table 1.

TABLE 1

Comparisons Between 'HGV25' and The Parent Plant.

| Characteristic | 'HGV25' | The Parent Plant. |
|---|---|---|
| Growth habit. | Wider but shorter than the parent plant. | More compact in diameter but taller than 'HGV23'. |

TABLE 1-continued

Comparisons Between 'HGV25' and The Parent Plant.

| Characteristic | 'HGV25' | The Parent Plant. |
|---|---|---|
| Prescence and shape of variegation on the mature foliage's abaxial surface. | More prominent than the parent plant. Green with a blend of very light green and greyed-green adjacent to the main vein and greyed-green along the interveinal areas of the distal half of the lamina. | Less prominent than 'HGV25'. The shape of variegation in the parent plant is alternating swathes of light green and dark green. No Prescence of a banded midrib. |
| General coloration of the mature foliage; abaxial surface. | Greyed-green. | Dark purple with lighter greyed-green to greyed-purple irregularly shaped triangles in an alternating pattern widening distally from the midrib. |

Comparisons with the closest known comparator: Plants of the new cultivar 'HGV25' differ from its closest known comparator, a *Calathea lietzei* plant named 'HGV24' (not patented), by the characteristics described in Table 2.

TABLE 2

Comparisons Between 'HGV25' and 'HGV24'

| Characteristic | 'HGV25' | 'HGV24' |
|---|---|---|
| Plant height and diameter | Larger than 'HGV24'. 18.1 cm in height and 33.1 cm in diameter, on average. | Smaller than 'HGV25'. 16.9 cm in height and 37.3 cm in diameter, on average. |
| Leaf size and shape. | Smaller than 'HGV24', elliptic to narrow ovate in shape and on average 14.2 cm in length and 6.1 cm in width. | Larger than 'HGV25', Broad elliptic to oblong in shape and on average 18.1 cm in length and 11.7 cm in width. |
| General coloration | More prominent than the parent plant. Green with a blend of very light green and greyed-green adjacent to the main vein and greyed-green along the interveinal areas of the distal half of the lamina. | Yellow-green to greyed-green laminas with a pink overlay proximal to the point of an attachment and an alternating arrangement of green and yellow-green variegation expressed as irregularly outlined lanceolate-shaped blotches extending outward from both sides of the midrib, approximately 50 percent towards the margins. The margins are splotched and marbled green. |
| of the mature foliage; adaxial surface. | | |
| General coloration of the mature foliage; abaxial surface. | Greyed-green. | Greyed-purple, with an overtone of greyed-purple variegation beside the lateral venation. |
| Venation color, adaxial surface. | The midrib is yellow-green, and the lateral veins are green. | The midrib is greyed-orange, proximally to the point of attachment is an overtone of greyed-red. Distally the color transitions to yellow-green. Lateral veins are green. |
| Venation color, abaxial surface. | The midrib is yellow-green, becoming lighter proximally to the point of attachment. Lateral veins are greyed-green. | The midrib is greyed-red and the lateral veins are greyed-purple. |

That which is claimed is:

1. A new and distinct variety of *Calathea* plant named 'HGV25', substantially as described and illustrated herein.

* * * * *